(12) United States Patent
Barrier et al.

(10) Patent No.: US 8,613,740 B2
(45) Date of Patent: Dec. 24, 2013

(54) HAND-HELD MANIPULATOR WITH SYMMETRICAL GRIP

(75) Inventors: Pascal Barrier, Annecy (FR); Jérémy Ollagnier, Meythet (FR); Rémi Rosset-Lanchet, Annecy (FR)

(73) Assignee: Dexterite Surgical, Annecy (FR)

( * ) Notice: Subject to any disclaimer, the term of this patent is extended or adjusted under 35 U.S.C. 154(b) by 0 days.

(21) Appl. No.: 13/387,786

(22) PCT Filed: Jul. 30, 2010

(86) PCT No.: PCT/IB2010/053473
§ 371 (c)(1),
(2), (4) Date: Jan. 30, 2012

(87) PCT Pub. No.: WO2011/013100
PCT Pub. Date: Feb. 3, 2011

(65) Prior Publication Data
US 2012/0130356 A1   May 24, 2012

(30) Foreign Application Priority Data
Jul. 31, 2009   (FR) ...................................... 09 55385

(51) Int. Cl.
*A61B 19/00* (2006.01)
*A61B 17/00* (2006.01)

(52) U.S. Cl.
USPC ................... 606/1; 81/177; 81/489; 408/131; 451/557

(58) Field of Classification Search
None
See application file for complete search history.

(56) References Cited

U.S. PATENT DOCUMENTS

| | | |
|---|---|---|
| 5,618,294 A | 4/1997 | Aust |
| 6,187,026 B1 | 2/2001 | Devlin |
| 6,391,046 B1 | 5/2002 | Overaker |
| 7,004,957 B1 | 2/2006 | Dampney |
| 2004/0225256 A1* | 11/2004 | Ponzi et al. ................. 604/95.04 |
| 2006/0241567 A1 | 10/2006 | Schaffer |
| 2007/0185486 A1 | 8/2007 | Hauck |
| 2009/0163943 A1* | 6/2009 | Cavanaugh et al. .......... 606/180 |
| 2009/0171275 A1* | 7/2009 | Ostrovsky et al. ......... 604/95.04 |

FOREIGN PATENT DOCUMENTS

FR     2875282 A1     3/2006

* cited by examiner

Primary Examiner — Sam Yao
Assistant Examiner — Scott T Luan
(74) Attorney, Agent, or Firm — William H. Eilberg

(57) ABSTRACT

A hand-held manipulator includes a handle (4) fixedly mounted on the end of a connecting arm (2), the distal end (2b) of which carries a work unit (3). The handle (4) includes a grip section (4e) having a surface of revolution about a longitudinal handle axis (III), which is aligned with the longitudinal axis (I) of the arm. Control elements (4a-4c) are shaped in an annular structure near the distal end (4f) of the grip section (4e) so as to be accessible in any angular orientation of the hand holding the handle.

13 Claims, 4 Drawing Sheets

HAND-HELD MANIPULATOR WITH SYMMETRICAL GRIP

TECHNICAL FIELD OF THE INVENTION

The present invention relates to manipulation devices, permitting the movements of a manipulation instrument located inside an operating area to be controlled from outside the operating area.

In particular, said manipulation devices permit a surgical tool to be positioned and controlled in applications for minimally-invasive surgery carried out by endoscopy.

In said applications, it is necessary to be able to displace and control a surgical tool to carry out various operations such as providing a suture, tying a knot or delicate dissection of tissue. These are intricate, precise operations in which the movements to be carried out are complex.

The invention relates more specifically to portable, articulated surgical manipulation devices in which a surgical tool is placed at the end of a portable manipulator, essentially having a connecting arm with a proximal end and a distal end. A proximal end of the connecting arm carries a control unit having a handle capable of being held by one hand. A working unit is mounted on the distal end of the connecting arm and comprises a tool support capable of supporting a tool or carrying the tool.

Simple, portable, articulated surgical instruments comprise, in the control unit, a control member of which the activation causes the inclination of the tool support and the tool by one degree of freedom of distal orientation about a transverse axis. More specifically, the operations to be carried out generally require the tool to describe the entire solid angle formed by a cone covering the distal end of the connecting arm in order to orientate the tool in the correct position for the operation to be carried out, or to drive the tool during this operation.

In the majority of existing portable articulated manipulators, the position of the hand of the operator is fixed to the handle of the manipulator and generally a plurality of mechanical or motorized means are provided for controlling the inclination of the tool relative to the longitudinal axis of the connecting arm and the orientation of the direction of this inclination about the longitudinal axis of the connecting arm. This requires the device to be complicated, however, by providing a motor or other mechanical system, mechanical connecting means and joints.

With the existing handles, the operator is not able to modify the grip of his/her hand on the handle, and the capacity for rotation of the handle is thus limited to a value of a few tens of degrees corresponding to the amplitude of possible movements of the wrist joint of the hand holding the manipulator. The amplitude of the movement of the wrist joint is, moreover, dependent on the initial position of the wrist which holds the manipulator. This capacity for movement is clearly insufficient for the tool to carry out at the end of the manipulator all the operations generally envisaged.

The document U.S. Pat. No. 6,187,026 B1 discloses a manipulator, comprising:
- a control unit having a handle capable of being held by one hand,
- at least one control member mounted on the handle and capable of being activated by at least one finger of the hand holding the handle,
- a connecting arm extending along a longitudinal axis of the arm, having a proximal end in which the control unit with the handle is mounted, and having a distal end,
- a working unit mounted on the distal end of the connecting arm, comprising a tool support carrying a forceps-type tool and able to be actuated by said at least one control member to open and close the forceps, and in which:
- the handle comprises a gripping portion having a gripping surface about a longitudinal axis of the handle, which is shaped so as to allow the same manual gripping in any angular orientation about the longitudinal axis of the handle and to permit a uniform rotation of the handle in the hand or between the fingers,
- the handle is fixed to the proximal end of the connecting arm,
- the longitudinal axis of the handle is colinear with the longitudinal axis of the arm,
- said at least one control member is shaped so as to be accessible about the handle in a continuous annular control area in the vicinity of the distal end of the gripping portion, whatever the orientation of the hand about the longitudinal axis of the handle.

Due to this arrangement, the operator is able to displace his/her hand on the handle, release the palm from the handle and roll the manipulator in the palm of the hand or between the thumb and the other fingers, so as to apply a relative axial rotational movement to the manipulator along the longitudinal axis of the connecting arm. At the same time, by the particular arrangement of the control member(s) which remain accessible in an annular control area, the operator is able to activate permanently the control member(s) to cause the opening and closing of the forceps.

Said device, however, has the drawback of not being able to orientate the forceps outside the longitudinal axis, nor to be able to apply to the forceps a specific rotation about the axis thereof when said axis is inclined outside the longitudinal axis of the manipulator.

SUMMARY OF THE INVENTION

The object of the present invention is to design a manipulator in which the operator is able to apply to the manipulator in a simple and manual manner a relative axial rotational movement about the longitudinal axis of the connecting arm relative to the hand which holds the manipulator, without necessarily losing the permanent capacity for holding the tool in position and activating the control member(s) mounted on the handle to permit relative movements of the tool support and/or of the tool at the distal end of the connecting arm to be controlled.

In order to achieve said objects and other objects, it is provided that the tool support and tool are able to be actuated by the control members in at least one specific rotational movement of the tool in the direction of inclination, by a rotation of the "screwdriver" type. Thus, it is possible to create in a simple manner all the necessary movements of the tool for the operations envisaged.

Preferably, the actuation of a control member activates a specific rotation actuator housed in the control body which drives the working unit to provide the tool with the specific rotational movement.

According to an advantageous embodiment, the tool support and the tool are also able to be actuated by the control members in at least one lateral inclination movement of adjustable amplitude in a direction of inclination. This is a capacity for movement which is very useful for the operations envisaged. In practice, it is possible to provide that the actuation of a further control member activates an inclination actuator housed in a control body which drives the tool support in an inclined movement.

According to a first embodiment, the gripping portion has a cylindrical revolution shape. This is the simplest shape, which is easily able to be implemented and adapted to any size of operator hand.

According to a further embodiment, the gripping portion has a pear-shaped revolution shape, the diameter of the gripping portion increasing progressively from the distal end to the proximal end, with a rounded proximal end. Thus the grip is improved and the increase in diameter also makes it possible to increase the precision of the angular positioning of the manipulator about the longitudinal axis of the connecting arm.

As an alternative, the gripping surface of the handle may have a polygonal cross section with a sufficient number of sides for a uniform grip and/or may have superficial irregularities such as a non-slip knurled surface, a grooved surface, etc.

In all cases, the gripping surface is contained within an envelope having a revolution shape about the longitudinal axis of the handle.

According to an embodiment, said at least one control member comprises a ring which may be urged in rotation about the longitudinal axis of the handle and/or in axial translation along the longitudinal axis of the handle.

As an alternative, said at least one control member comprises a series of buttons distributed in an annular and uniform manner about the longitudinal axis of the handle and operatively coupled together to produce the same actuation of the working unit.

According to both alternatives, it is possible to provide a plurality of control members, offset relative to one another along the longitudinal axis of the handle, in the vicinity of the distal end of the gripping portion.

Preferably, the control members have respective annular envelopes of which the respective diameters increase in the direction of the distal end of the handle.

Preferably, in the case of a forceps-type tool, the manipulator further comprises a control member capable of controlling the opening and closing of the tool.

According to an advantageous embodiment, the manipulator is also able to comprise, on the peripheral surface of the control unit, a locator of the angular position about the longitudinal axis of the connecting arm.

For example, the locator of the angular position is a superficial irregularity of the peripheral surface of the handle, perceptible by the hand holding the handle. In this manner, the operator is able to locate the orientation of the tool in the operating area, and verify the information received from the endoscope.

BRIEF DESCRIPTION OF THE DRAWINGS

Further subjects, features and advantages of the present invention will emerge from the following description of particular embodiments, made with reference to the accompanying figures, in which.

DESCRIPTION OF PREFERRED EMBODIMENTS

Figure 1:
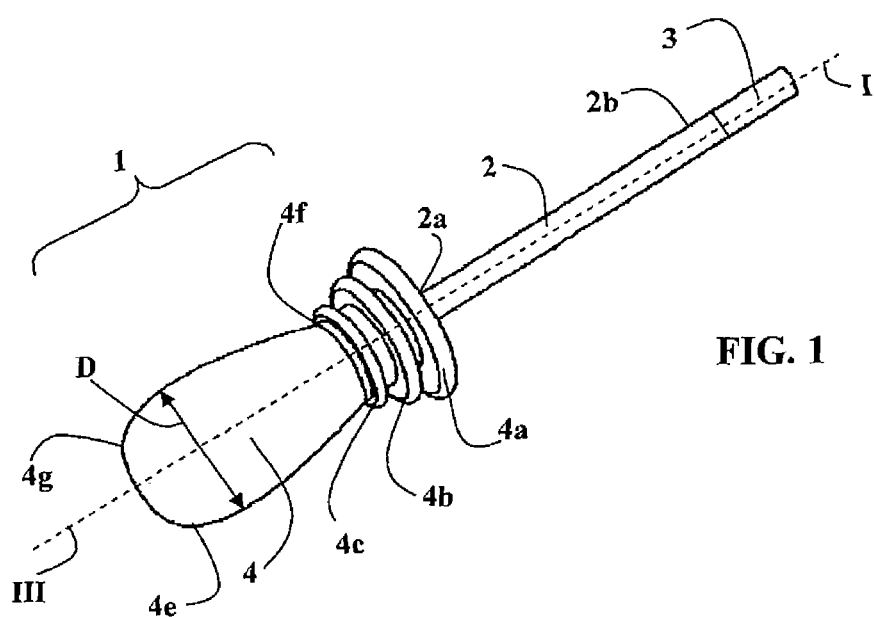
FIG. 1 is a perspective view of a manipulator according to a first embodiment of the present invention.
Figure 2:
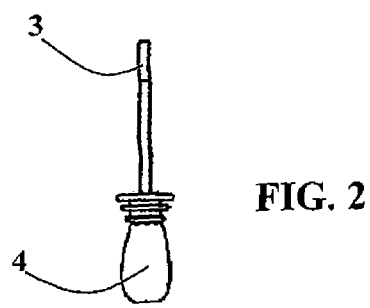
FIG. 2 is a front view of the manipulator of FIG. 1.
Figure 3:
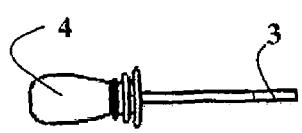
FIG. 3 is a side view of the manipulator of FIG. 1.
Figure 4:
FIG. 4 is an end view of the manipulator of FIG. 1.
Figure 5:
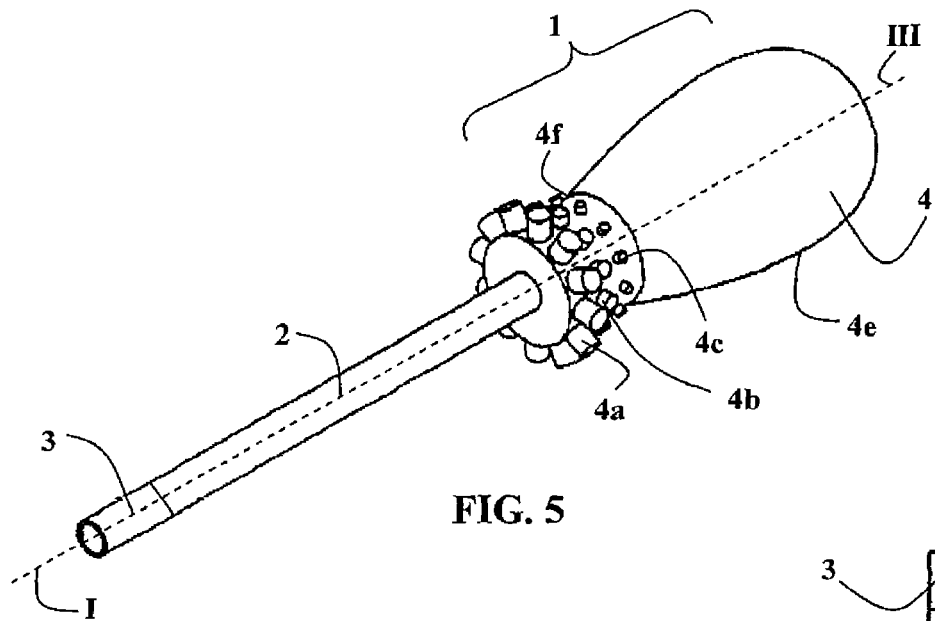
FIG. 5 is a perspective view of a manipulator according to a second embodiment of the present invention.

In the embodiments illustrated in the figures, a manipulator according to the invention comprises a control unit 1 having a handle 4 which is capable of being held by one hand.

The handle 4 carries at least one control member, for example three control members 4a, 4b and 4c, the control members being structured and arranged so as to be able to be activated by at least one finger of the hand holding the handle 4.

The manipulator comprises a connecting arm 2 extending along a longitudinal axis of the arm I, having a proximal end 2a and a distal end 2b.

The control unit 1 is mounted in the proximal end 2a of the connecting arm 2 and the handle 4 forms the proximal end of the manipulator.

Figure 9:
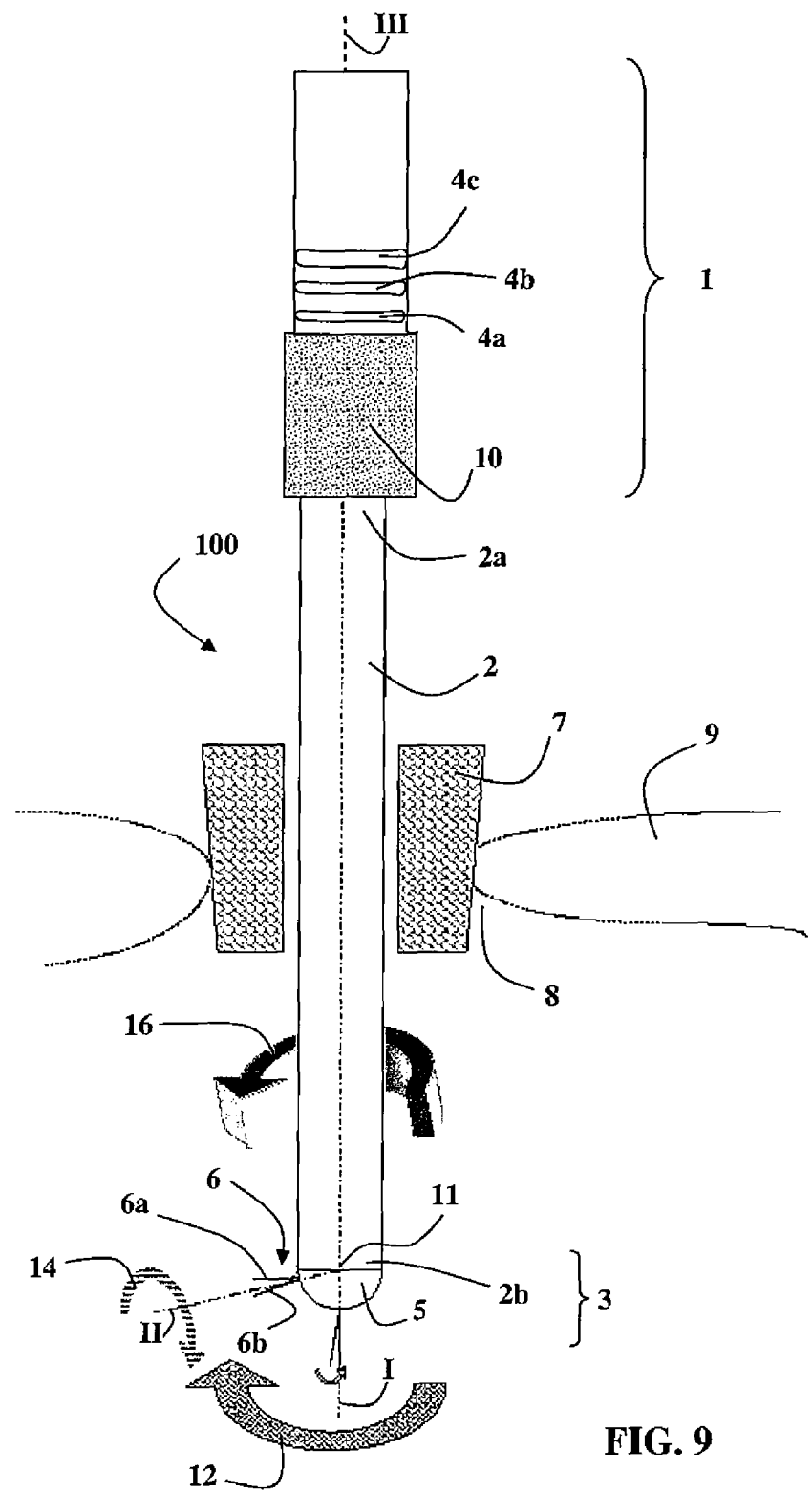
FIG. 9 is a schematic side view of a manipulator according to a further embodiment of the present invention.

In FIG. 9, the manipulator is illustrated in the position of use. As in the known devices, the connecting arm 2 passes into a trocar 7, providing the connection and passage into an opening 8 made in the body wall 9 of a patient.

A working unit 3 is mounted on the distal end 2b of the connecting arm 2 and comprises a tool support 5, carrying, or capable of receiving, a tool 6 and able to be actuated by said at least one control member 4a-4c, according to at least one degree of freedom of movement.

The handle 4 comprises a gripping portion 4e having a gripping surface about a longitudinal axis of the handle III.

In the embodiments illustrated in FIGS. 1 to 8, the gripping portion 4e has a pear-shaped revolution shape, the diameter D of the gripping portion 4e increasing progressively from the distal end 4f to the proximal end 4g. The proximal end 4g is itself rounded, for example spherical cap-shaped.

Figure 10:
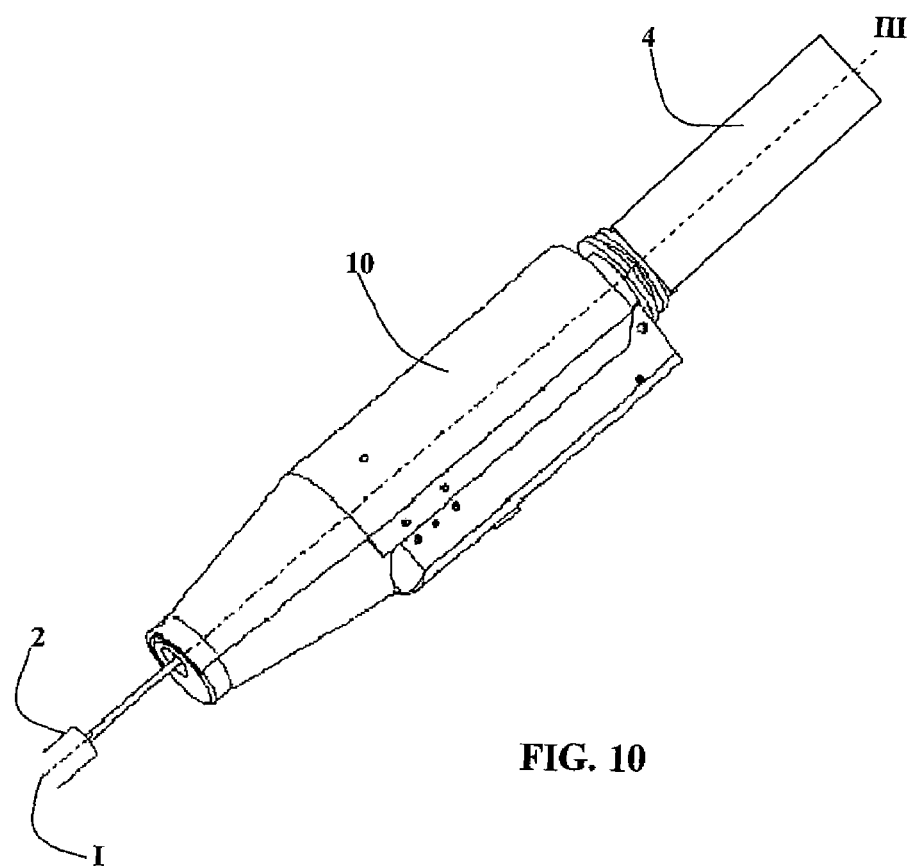
FIG. 10 is a perspective view of a variant of the manipulator of FIG. 9.

In the embodiment of FIGS. 9 and 10, the gripping portion 4e has a cylindrical revolution shape.

Figure 11:
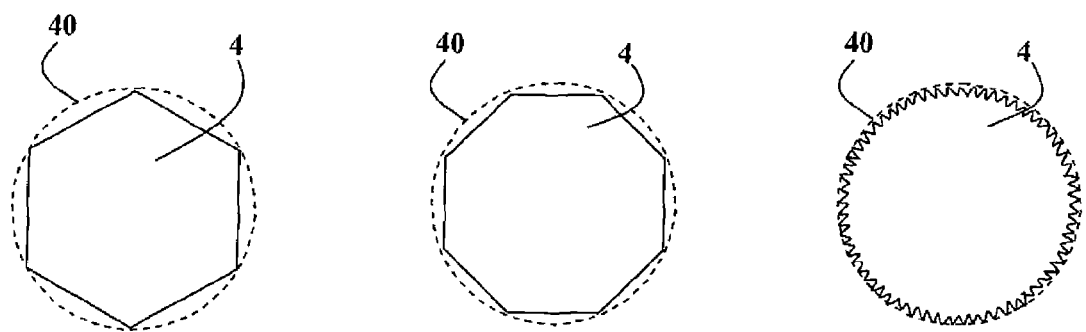
FIG. 11 illustrates the cross section of a manipulator handle according to three variants of the invention.

In the embodiments illustrated by way of example in cross section in FIG. 11, the gripping portion has a hexagonal cross section in the left-hand view, or an octagonal cross section in the central view, or a circular grooved cross section in the right-hand view, and each time the envelope 40 has been shown in dashed lines.

In all the embodiments, the gripping surface of the gripping portion 4e has a shape contained in an envelope, such as the envelope 40 illustrated in dashed lines, which itself has a revolution shape about the longitudinal axis of the handle III. This permits the same gripping by the hand or fingers in all angular orientations about the longitudinal axis of the handle III and permits a regular rotation of the handle 4 in the hand of the operator or between the fingers.

In all the embodiments, the handle 4 is fixed to the proximal end 2a of the connecting arm 2 and the longitudinal axis of the handle III is colinear with the longitudinal axis of the arm I.

The structure of the control members 4a-4c will now be considered.

In the embodiment of FIGS. 1 to 4, 9 and 10, the control members 4a-4c each comprise a ring which may be urged in rotation about the longitudinal axis of the handle III or in axial translation along the longitudinal axis of the handle III.

The control members are arranged in a continuous annular area of control in the vicinity of the distal end 4f of the gripping portion 4e. In this manner, the hand portion which carries the manipulator is on the gripping portion 4e remote from the control members, said control members being capable of being activated by a finger of the hand which does not participate in the gripping of the handle.

In the embodiment of FIGS. 5 to 8, the control members 4a-4c each comprise a series of buttons distributed in an annular and uniform manner about the longitudinal axis of the handle III and operatively coupled together to produce the same actuation of the working unit 3. The control members 4a-4c with buttons are also arranged in the vicinity of the distal end 4f of the gripping portion 4e. All the buttons of each control member are contained in one respective annular envelope.

By this configuration and arrangement, the control members are accessible about the handle 4, whatever the orientation of the hand about the longitudinal axis of the handle III.

In the embodiments illustrated in the figures, comprising three control members, the control members 4a-4c are offset from one another along the longitudinal axis of the handle III, whilst remaining in the vicinity of the distal end 4f of the gripping portion 4e.

To facilitate the discrimination of the control members from one another, so that the operator is able to actuate individually any of the control members, the respective envelopes of the control members 4a-4c have different respective diameters, for example respective diameters which increase in the direction of the distal end of the handle 4, as illustrated in the figures.

Alternatively or in addition, the control members may be provided with a shape or distinctive surface state which the operator is able to recognize by touch: smooth surface, grooved surface longitudinally, grooved surface horizontally, wide surface, narrow surface, etc.

FIG. 9 is now considered, which illustrates in a more complete manner a manipulator structure according to an embodiment of the present invention.

In this embodiment, the tool support 5 and the tool 6 are able to be actuated by control members 4a-4c, in at least one lateral inclination movement 12 of adjustable amplitude in a direction of inclination II and a specific rotational movement 14 of the tool 6 about the direction of inclination II by a rotation of the "screwdriver" type.

For example, the activation of the first control member 4a of the handle 4 controls an inclination actuator housed in the control body 10 which itself drives the tool support 5 in an inclination movement 12 about a transverse axis of inclination 11. Thus, the tool support 5 and the tool 6 may adopt an inclination in which they are oriented in a direction of inclination II.

By the activation of the second control member 4b of the handle 4, a specific rotation actuator housed in the control body 10 is controlled which drives the tool support 5 or the tool in a specific rotational movement 14 about the inclination direction II.

By the actuation of the forceps control member 4c by the handle 4, a forceps actuator is controlled to achieve either the opening or the closing of the forceps 6.

Each of the actuators may be of the electric motor, hydraulic actuator or pneumatic actuator, mechanical transmission type, for example.

It is noteworthy, according to the invention, that the operator is easily able to apply to the manipulator an axial rotational movement about the longitudinal axis I of the connecting arm 2 by rotation of the handle 4 in the hand of the user, for example between the thumb and other fingers, in the manner of a screwdriver. This axial rotational movement makes it possible to orientate at will the direction of inclination II about the longitudinal axis of the arm I, such that it is possible in a simple manner to give the tool 6 any orientation within the cone which covers the distal end 2b of the longitudinal arm 2.

In the case where the tool 6 is forceps, the third control member 4c may advantageously control the opening and closing of the forceps.

Alternatively, the opening and closing of the forceps may be controlled by the actuation of a longitudinal lever articulated on the handle which is retracted in the forceps clamping position, thus permitting the capacity for rotation of the handle in the hand or between the fingers of the operator.

Figure 6:
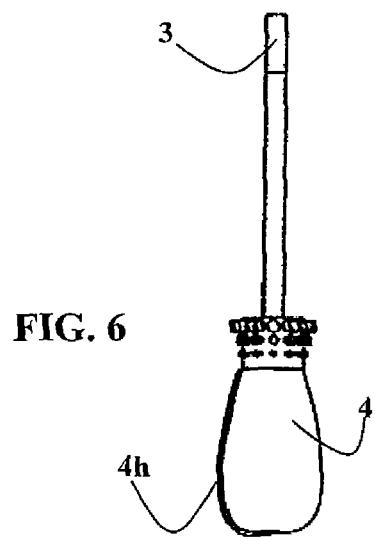
FIG. 6 is a front view of the manipulator of FIG. 5.
Figure 7:
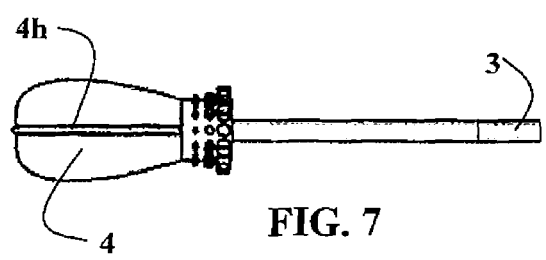
FIG. 7 is a side view of the manipulator of FIG. 5.
Figure 8:
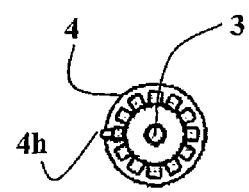
FIG. 8 is an end view of the manipulator of FIG. 5.

Due to the capacity of such a manipulator for rotation about the longitudinal axis I, it proves advantageous to provide the operator with a means of locating the angular position of the manipulator. To achieve this, as illustrated in FIGS. 6 to 8, it is possible to provide a locator of the angular position about the longitudinal axis I of the connecting arm 2.

In practice, in the illustrated embodiment, the locator of the angular position is a superficial irregularity of the peripheral surface of the handle 4, perceptible by the hand holding the handle. For example, this superficial irregularity may be a longitudinal rib 4h or a lever for clamping the forceps.

The present invention is not limited to the embodiments which have been specifically disclosed but includes different variants and generalizations contained within the scope of the following claims.

The invention claimed is:

1. A manipulator comprising:
   a control unit (1) having a handle (4) capable of being held by one hand,
   at least one control member (4a-4c) mounted on the handle (4) and capable of being activated by at least one finger of the hand holding the handle (4),
   a connecting arm (2) extending along a longitudinal axis of the arm (I), having a proximal end (2a) in which the control unit (1) with the handle (4) is mounted, and having a distal end (2b),
   a working unit (3) mounted on the distal end (2b) of the connecting arm (2), comprising a tool support (5) carrying, or capable of receiving, a surgical tool (6) and able to be actuated by control members (4a-4c) according to at least one degree of freedom of movement,
   in which:
   the handle (4) comprises a gripping portion (4e) having a gripping surface about a longitudinal axis of the handle (III) which is shaped so as to allow a same manual gripping in any angular orientation about the longitudinal axis of the handle (III) and to permit a uniform rotation of the handle (4) in the hand or between the fingers,
   the handle (4) is fixed to the proximal end (2b) of the connecting arm (2),
   the longitudinal axis of the handle (III) is colinear with the longitudinal axis of the arm (I),
   said control members (4a-4c) are shaped so as to be accessible about the handle (4) in an annular control area in the vicinity of one end (4f) of the gripping portion (4e), whatever the orientation of the hand about the longitudinal axis (III) of the handle (4),
   wherein the working unit (3) is able to be actuated by a first control member (4a) of said control members (4a-4c) in at least one lateral inclination movement (12) of adjustable amplitude, so that the working unit (3) adopts an inclination in which it is oriented in a direction of inclination (II) with respect to the longitudinal axis of the arm (I), wherein the working unit (3) is able to be actuated by a second control member (4b) of the control members (4a-4c) according to at least one specific rotational movement (14) of the tool (6) about the direction of inclination (II), and wherein actuation of said second control member 4(b) activates a specific rotation motor housed in the control body (10) which drives the working unit (3) to provide the tool (6) with the specific rotational movement (14) about the direction of inclination (II).

2. The manipulator as claimed in claim 1, wherein the gripping portion (4e) has a cylindrical revolution shape.

3. The manipulator as claimed in claim 1, wherein the gripping portion (4e) has a pear-shaped revolution shape, the diameter (D) of the gripping portion (4e) increasing progressively from the distal end (4f) to the proximal end (4g), with a rounded proximal end (4g).

4. The manipulator as claimed in claim 1, wherein at least one of said control members (4a-4c) comprises a ring which may be urged in rotation about the longitudinal axis of the handle (III) and in axial translation along the longitudinal axis of the handle (III).

5. The manipulator as claimed in claim 1, wherein at least one of said control members (4a-4c) comprises a series of buttons distributed in an annular and uniform manner about the longitudinal axis of the handle (III) and operatively coupled together to produce a same actuation of the working unit (3).

6. The manipulator as claimed in claim 1, wherein a plurality of said control members (4a-4c) are offset relative to one another along the longitudinal axis of the handle (III) in the vicinity of the distal end (4f) of the gripping portion (4e).

7. The manipulator as claimed in claim 6, wherein the control members (4a-4c) have respective annular envelopes of which the respective diameters increase in the direction of the distal end (4f) of the handle (4).

8. The manipulator as claimed in claim 6, wherein the control members (4a-4c) have a shape or distinctive surface state which the operator is able to recognize by touch.

9. The manipulator as claimed in claim 1, comprising a forceps control member (4c) capable of controlling the opening and closing of a forceps-type tool (6).

10. The manipulator as claimed in claim 1, further comprising, on the peripheral surface of the control unit (1), a locator of the angular position (4h) about the longitudinal axis (I) of the connecting arm.

11. The manipulator as claimed in claim 10, wherein the locator of the angular position (4h) is a superficial irregularity of the peripheral surface of the handle, perceptible by the hand holding the handle (4).

12. The manipulator as claimed in claim 1, wherein at least one of said control members (4a-4c) comprises a ring which may be urged in rotation about the longitudinal axis of the handle (III) or in axial translation along the longitudinal axis of the handle (III).

13. A manipulator comprising:
a control unit (1) having a handle (4) capable of being held by one hand,
at least one control member (4a-4c) mounted on the handle (4) and capable of being activated by at least one finger of the hand holding the handle (4),
a connecting arm (2) extending along a longitudinal axis of the arm (I), having a proximal end (2a) in which the control unit (1) with the handle (4) is mounted, and having a distal end (2b),
a working unit (3) mounted on the distal end (2b) of the connecting arm (2), comprising a tool support (5) carrying, or capable of receiving, a surgical tool (6) and able to be actuated by control members (4a-4c) according to at least one degree of freedom of movement,
in which:
the handle (4) comprises a gripping portion (4e) having a gripping surface about a longitudinal axis of the handle (III) which is shaped so as to allow a same manual gripping in any angular orientation about the longitudinal axis of the handle (III) and to permit a uniform rotation of the handle (4) in the hand or between the fingers,
the handle (4) is fixed to the proximal end (2b) of the connecting arm (2),
the longitudinal axis of the handle (III) is colinear with the longitudinal axis of the arm (I),
said control members (4a-4c) are shaped so as to be accessible about the handle (4) in an annular control area in the vicinity of one end (4f) of the gripping portion (4e), whatever the orientation of the hand about the longitudinal axis (III) of the handle (4),
wherein the working unit (3) is able to be actuated by a first control member (4a) of said control members (4a-4c) in at least one lateral inclination movement (12) of adjustable amplitude, so that the working unit (3) adopts an inclination in which it is oriented in a direction of inclination (II) with respect to the longitudinal axis of the arm (I),
wherein the working unit (3) is able to be actuated by a second control member (4b) of the control members (4a-4c) according to at least one specific rotational movement (14) of the tool (6) about the direction of inclination (II),
wherein actuation of said second control member 4(b) activates a specific rotation motor housed in the control body (10) which drives the working unit (3) to provide the tool (6) with the specific rotational movement (14) about the direction of inclination (II), and
wherein the actuation of said first control member (4a) controls an inclination actuator housed in a control body (10) which drives the working unit (3) to provide the tool (6) with the inclination movement (12).

* * * * *